US005236415A

United States Patent [19]

Stallings

[11] Patent Number: 5,236,415

[45] Date of Patent: Aug. 17, 1993

[54] DRINKING STRAW FOR INGESTING UNPALATABLE LIQUIDS AND METHOD OF USE

[76] Inventor: Ronald V. Stallings, P.O. Box 18337, San Jose, Calif. 95158

[21] Appl. No.: 843,535

[22] Filed: Feb. 28, 1992

Related U.S. Application Data

[63] Continuation-in-part of Ser. No. 611,756, Dec. 31, 1990, abandoned.

[51] Int. Cl.[5] .............. A61M 31/00

[52] U.S. Cl. .............. 604/54; 604/77

[58] Field of Search .............. 604/49, 54, 77, 78, 604/79

[56] References Cited

U.S. PATENT DOCUMENTS

| | | | |
|---|---|---|---|
| 2,969,064 | 1/1961 | Metz | 604/77 |
| 3,572,337 | 3/1971 | Schunk | 604/77 |
| 3,637,141 | 1/1972 | Gores | 604/77 X |
| 3,747,595 | 7/1973 | Grossan | 604/77 X |
| 4,332,250 | 6/1982 | Behney | 604/54 |

FOREIGN PATENT DOCUMENTS

| | | | |
|---|---|---|---|
| 0388630 | 1/1924 | Fed. Rep. of Germany | 604/79 |

*Primary Examiner*—Gene Mancene
*Assistant Examiner*—Jeffrey A. Smith
*Attorney, Agent, or Firm*—Ronald V. Stallings

[57] ABSTRACT

A device for preventing an unpalatable liquid from reaching tastebuds of a user ingesting the liquid which includes a straw with open ends and a sponge positioned adjacent to one of the open ends. In preparation for use, the sponge is dipped into a flavorful drink then placed in the user's mouth with the open end of the straw at the rear of the mouth remote from the taste buds which are located in the tip of the tongue at the front of the mouth. The sponge, saturated with flavorful liquid, prevents the unpalatable liquid from reaching the tastebuds which are located at the tip of the tongue. The unpalatable liquid goes directly into the gullet. The tube may be flexible or have a flexible section for greater convenience. A screen may be provided which shields the container of unpalatable liquid from the view of the user.

17 Claims, 3 Drawing Sheets

DRINKING STRAW FOR INGESTING UNPALATABLE LIQUIDS AND METHOD OF USE

CROSS REFERENCE TO PRIOR APPLICATIONS

This application is a continuation-in-part to application Ser. No. 611,756 filed Dec. 31, 1990, now abandoned, for which priority is claimed.

BACKGROUND

1. Field of the Invention

This invention relates to devices intended to aid a user ingesting unpalatable liquids and particularly to a drinking straw that has been modified to shield the taste buds of the user from the ingested liquid.

2. Prior Art and Information Disclosure Statement

A number of treatments include orally administering medicine that is unpalatable to the patient. This is particularly true of patients who have ingested poison wherein a common treatment is to have the patient ingest a liquid containing a heavy concentration of activated carbon which absorbs the poison when it enters the stomach. The carbon must be administered as a gritty unadulterated powder with just enough liquid added to enable drawing the carbon through a straw in order that it be most effective as an absorber of the poison. The unpalatable taste and consistency of the carbon liquid very often causes the patient to gag or vomit.

In view of these problems and other situations involving ingestion of unpalatable liquids, numerous devices have been disclosed which are intended to disguise the taste of the liquid.

For example, U.S. Pat. No. 3,730,737 to Harvey is for a tip attached to an end of a straw wherein the tip contains a taste modifier, miraculin, combined with an ingredient that effervesces when contacted by a mild acid such as are found in drinks. The miraculin in the tip is coated to protect it from degradation that would result from its exposure to the atmosphere. When the tip is placed in the mouth and the drink is drawn through the straw, the drink contacts the tip, dissolves the coating and combines with the miraculin which thereby sweetens the drink.

U.S. Pat. No. 3,545,980 to Stanger is for a drinking straw with a candy tip formed on one end. When the user places the candy tip in his mouth, the candy dissolves and combines with liquid drawn through the straw thereby modifying the taste of the drink.

U.S. Pat. No. 3,463,361 to Cook et al is for a "self-contained device for adding one or more flavors to a liquid during intake by the drinker". The device is a drinking straw with a small auxilliary tube attached to and in communication with the main straw. Before use, flavoring material is placed in the auxilliary straw. When the main straw is inserted into a receptacle containing liquid and the user draws on its outlet end, the aspirator effect of the liquid passing the small aperture interconnecting the two straws has the effect of drawing the flavoring material into the liquid to flavor it.

The literature also discloses straws made of paper impregnated with flavoring compounds.

For example, U.S. Pat. No. 3,615,595 to Guttag is for a flavored drinking straw having at least a portion of an exposed wall formed of a water insoluble polymer. A water soluble flavoring agent is dispersed within the polymer. When the user draws on the straw, the flavoring passes directly into the liquid drawn through the straw.

U.S. Pat. No. 2,812,257 to Sisorek discloses a paper strip impregnated with a flavoring compound which is inserted into the straw such that liquid drawn through the straw is flavored as it passes over the paper.

All of the aforementioned inventions are devices which modify the taste of the ingested liquid. They operate by mixing the ingested liquid with an appropriate flavoring compound. Therefore, they are only partially effective in improving the taste of the liquid.

Furthermore, they do nothing to disguise the texture of the ingested liquid such as may result from the presence of insoluble particulates in the liquid.

Another disadvantage presented by most all the inventions is that the selection of flavoring compounds is limited. Another disadvantage is that extreme precautions such as appropriate storage, etc. are required to preserve the flavored ingredients, prevent contamination and spoilage, etc.

Three inputs to the senses combine to produce the resultant sensation of taste. Once input is from the taste buds which are located in the front of the mouth close in the tip of the tongue. The second input is from smell. The third input is from sight. A problem with the activated carbon is that its jet black appearance is very offensive to a sick person attempting to swallow it for medicinal purposes.

THE INVENTION

Objects

It is an object of this invention to provide a modified drinking straw that enables a user to ingest an unplatable liquid and avoid the consequences of the bad taste. In an extreme example, these consequences would include nausea that would prevent him from drinking the liquid.

It is another object that the user experience a taste selected by him from a very large range of tastes that he will experience when drinking the liquid regardless of the actual taste of the unpalatabe liquid.

It is another object that the device have a long shelf life.

It is another object to prevent the unpalatable liquid from contacting the taste buds.

It is another object to prevent the user from being disturbed by the sight of the liquid.

It is another object that the device feel comfortable when positioned in the users mouth.

SUMMARY

This invention is directed toward a drinking straw provided on one end with a sponge. Before drinking an unpalatable liquid, the user dips the sponge into a flavorful liquid of his choice thereby saturating the sponge. He then places the sponge end of the straw in his mouth and draws in the unplatable liquid through the straw.

The sponge is shaped and dimensioned for conveniently placing the sponge in the patient's mouth with the open end of the straw and sponge at the rear of the mouth past the taste buds which are located in the front of the mouth. Therefore, when unpalatable liquid is drawn through the straw, it is prevented from reaching the tastebuds by the sponge soaked with tasteful liquid and so passes directly to the stomach.

In one embodiment, a cap on the end of the straw/-sponge acts as an additional barrier and aids in preventing unpalatable liquid passing out of the end of the straw from mixing with the tasteful liquid contained in the sponge.

In other embodiments, a disk positioned on the straw prevents the user from seeing the drink. To a poison victim, already sick from ingested poison, the sight of a jet black drink of activated carbon is very daunting and the disk alleviates this source of discomfort by shielding the drink from his view.

The straw may have a flexible section so that the user may withdraw the liquid with the flexible section bent while sitting, standing or lying in an otherwise awkward position.

DESCRIPTION OF THE PREFERRED EMBODIMENT

The following detailed description illustrates the invention by way of example and not by way of limitation of the principles of the invention. This description will clearly enable one skilled in the art to make and use the invention and describes several embodiments, adaptations, variations, alternatives and uses of the invention including what I presently believe to be the best mode for carrying out the invention.

Figure 1:
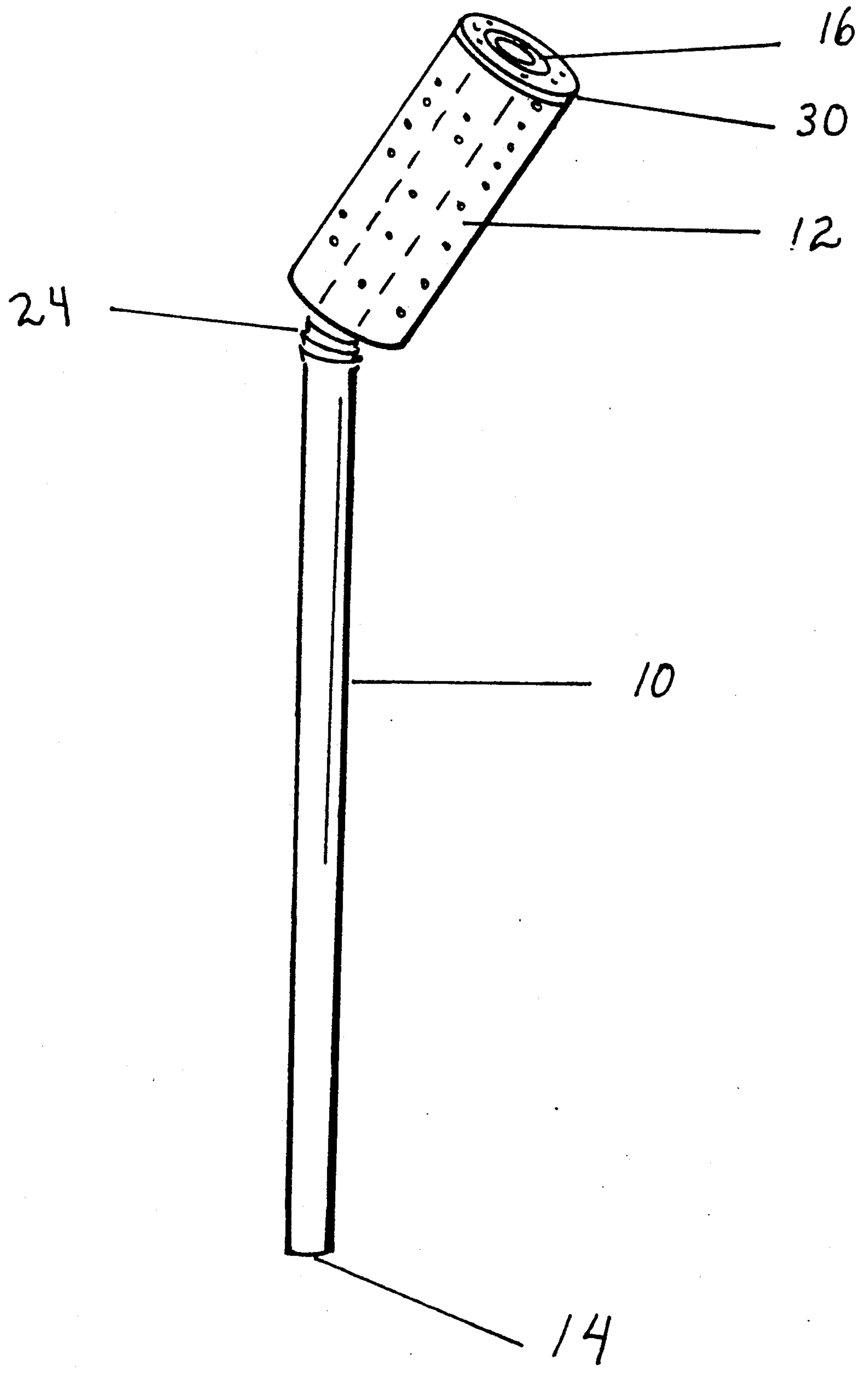
FIG. 1 shows a perspective view of the modified drinking straw of this invention.
Figure 2:
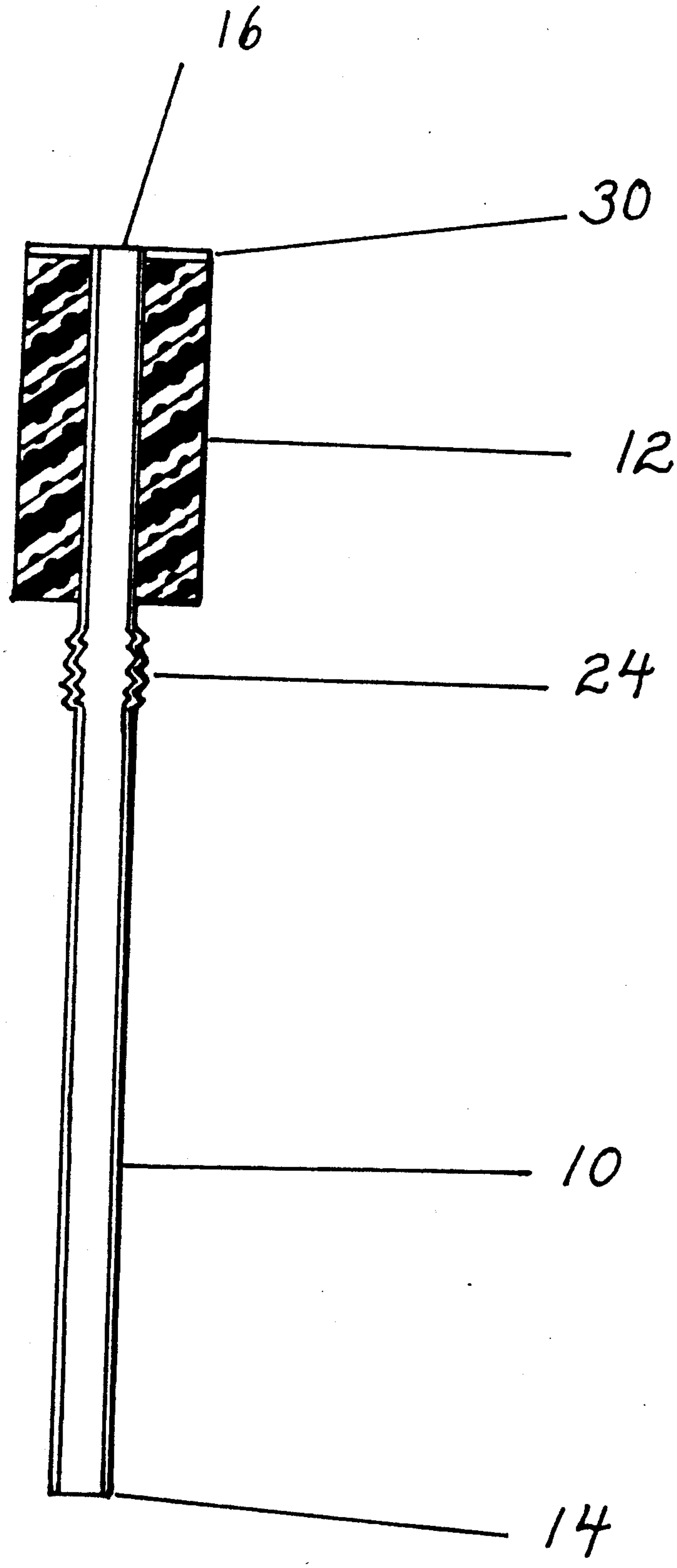
FIG. 2 is a cross sectional view of FIG. 1.

Turning now to a discussion of the drawings, FIG. 1 shows a perspective view of the modified drinking straw of this invention. FIG. 2 is a sectional view of FIG. 1. There is shown a straw 10 with one end 16 positioned through a sponge 12.

Figure 3:
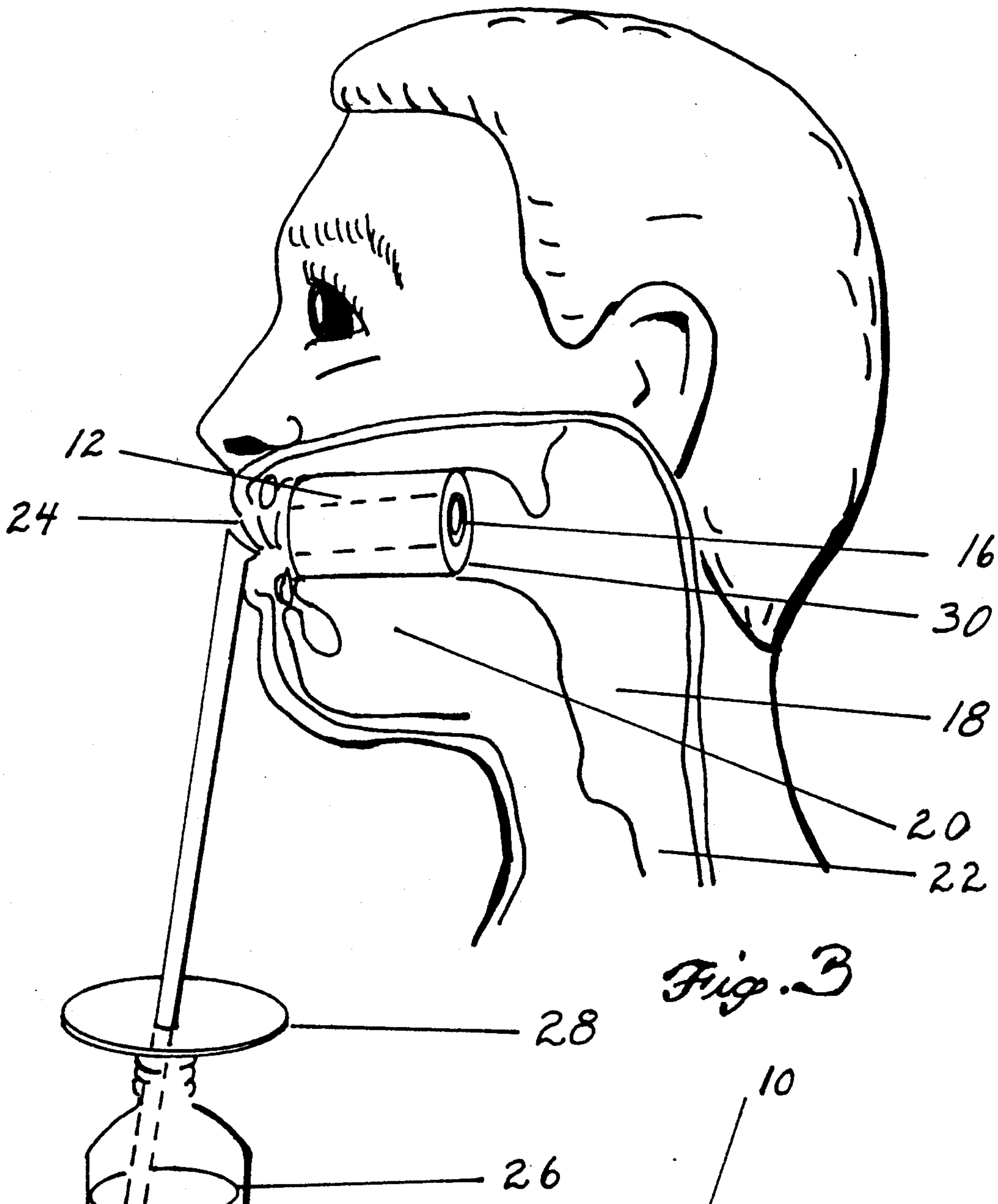
FIG. 3 shows the sponge end of the straw in a user's mouth.

When preparing to use the device, the sponge end 16 of the straw is first dipped into flavorful liquid which can be any common beverage—coffee, milk, soft drink, fruit juice,—selected by the user. Then, as shown in FIG. 3, the sponge end 16 of the straw is placed in the user's mouth with the end 16 positioned as far to the rear of the mouth (away from the tip of the tongue 20) as comfortable thereby avoiding the tastebuds at the tip of the tongue. This is illustrated in FIG. 3. Unpalatable liquid 18 is drawn through the open bottom end 14 and out of the top open end 16 of the straw. The sponge 12, saturated with flavorful liquid, effectively blocks the back flow of unpalatable liquid 18 to the tastebubs located at the tip of the tongue 20 so that the unpalatable liquid passes directly down the gullet 22. As shown in FIG. 3 as well as FIGS. 1 and 2, a short length 24 of straw 10 is flexible in order that the user may draw on the straw from a comfortable position with respect to the container 26 of the unpalatable liquid 18.

FIG. 3 also shows an embodiment of the invention where an opaque screen 28 is mounted on the straw in a position to shield the unpalatable liquid from the view of the user. This feature is particularly helpful in ameliorating the bad taste when the unpalatable liquid has an especially offensive appearance such as is the case with jet black activated carbon.

Figure 4:
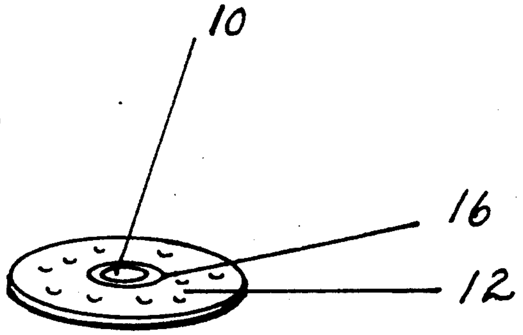
FIG. 4 shows an end view of the straw.

FIG. 4 shows an end view of the sponge end 16 of the straw illustrating that the cross sectional shape of the straw may be elliptical or any convenient shape to fit comfortably in the mouth. Furthermore, in contrast to the rigid constructions described in the Background, the sponge is soft and pliable thereby adding to the comfort of the user when placed in the user's mouth. In view of this, it may be noted that, in the absence (unavailability) of a flavorful liquid in which to dip the sponge, a dry sponge placed in the users mouth would offer some degree of comfort in preventing a portion of the unpalatable liquid from reaching the user's taste buds.

In an additional embodiment shown in FIGS. 1, 2 and 3, a latex cap 30 on the sponge 12 at the end 16 of the straw serves as an additional barrier to further inhibit backflow of the unpalatable liquid to the tip of the tongue 20.

The sponge may be made of anyone of a number of materials, e.g., rubber or foam of vinyl, urethane, etc. The straw may be plastic or paper or any convenient material. The modified straw is inexpensive to fabricate compared to a number of devices described in the prior art and therefore is disposable after use.

In the foregoing paragraphs, an embodiment has been described which meets the objects of the invention. The crux of the invention is a device which prevents an unpalatable liquid from reaching the tastebuds of a user when the user is ingesting the unpalatable liquid. This embodiment includes construction of a drinking straw that effectively shields an unpalatable liquid from the tastebuds of the user by imposing a barrier, the sponge soaked with flavorful liquid, between the taste buds at the tip of the tongue and end of the straw from which unpalatable liquid flow directly into the gullet. This action or construction clearly is not anticipated by the devices of the prior art which are constructed in a way such that the taste of the unpalatable liquid is changed to a greater or lesser degree by mixing the flavorful ingredient with the unpalatable liquid.

The user can select a liquid having a taste flavorful to him to saturate the sponge. The flavorful liquid may also be aromatic as further assurance that the taste of the unpalatable liquid is disguised. The flavorful liquid may also be aromatic as further assurance that the taste of the unpalatable liquid is disguised.

Since the straw may be stored before use in the dry state, there is no problem in having to store the device saturated with flavorful liquid. The screen shields the liquid from the view of the user. The flexible section of the straw makes ingesting the unpalatable liquid more convenient.

It should be understood that various modifications within the scope of this invention can be made without departing from the spirit thereof. For example, the straw could be made of two lengths of glass tubing joined by a short section of flexible vinyl tubing or the entire straw may be flexible vinyl tubing. I therefore wish my invention to be defined by the appended claims as broadly as the prior art will permit and in view of the specification if need be.

I claim:

1. A device for preventing an unpalatable liquid from reaching the taste buds of a user when the liquid is ingested by the user from a container the device comprising:

a straw means having an open first end and an open second end;

a means attached to said second end of said straw means for preventing said unpalatable liquid flowing out of said second end, when said second end is placed at the back of a mouth of a user, from flowing toward a front of said mouth thereby causing said unpalatable liquid to flow down a gullet of said user without contacting the tastebuds at said front of said mouth of said user, wherein said means for preventing comprises a sponge.

2. A device as in claim 1 wherein said straw means is a tube.

3. A device as in claim 2 wherein said tube is made of material selected from a group that consists of paper and plastic.

4. A device as in claim 2 wherein said tube is flexible.

5. A device as in claim 2 which further comprises an opaque screen means secured to said tube for shielding said container of unpalatable liquid from view of said user.

6. A device as in claim 1 wherein said sponge is pliable.

7. A device as in claim 6 wherein said sponge has a shape selected to conform to said user's mouth.

8. A device as in claim 7 wherein said shape has a cylindrical cross section with an axis substantially concentric with said straw means.

9. A device as in claim 8 wherein said shape has an elliptical cross section with an axis substantially concentric with said straw means.

10. A device as in claim 6 wherein said sponge is made from a material selected from the group that consists of rubber, vinyl and urethane.

11. A device as in claim 10 wherein said straw means is a flexible vinyl tube.

12. A device as in claim 1 wherein said sponge is saturated with a flavorful liquid.

13. A device as in claim 12 wherein said flavorful liquid is aromatic.

14. A device as in claim 1 wherein said sponge has a first end and a second end adjacent to said second end of said straw means and said device comprises a cap means positioned in operable combination with said second ends of said straw and sponge for inhibiting backflow of said unpalatable liquid from said second end of said straw means to said sponge second end.

15. A device as in claim 1 wherein said straw means comprises a section located between said first and second straw ends that is flexible thereby providing that said second end of said straw means can be placed in the mouth of a user in a position that is comfortable relative to a container of said unpalatable liquid.

16. A device as in claim 1 wherein said straw means is a tube made of material selected from the group that consists of paper, plastic and glass.

17. A method for preventing an unpalatable liquid ingested by a user from reaching the taste buds when drawing the unpalatable liquid from a container which includes the steps:

dipping into a flavorful liquid a first open end of a device wherein said device includes a hollow tube having a first end and a sponge positioned adjacent to said first end of said tube thereby saturating said sponge with said flavorful liquid;

placing said first end of said hollow tube and sponge into a mouth of said user with said first end positioned at a back of said mouth;

placing a second open end of said hollow tube into a reservoir of said unpalatable liquid;

drawing said unpalatable liquid from said reservoir, through said hollow tube and out of said first open tube end providing that said unpalatable liquid will pass directly into a gullet of said user and will be prevented from contacting tastebuds located in a front of said mouth by said sponge.

* * * * *